United States Patent
Busscher et al.

(10) Patent No.: US 11,510,865 B2
(45) Date of Patent: Nov. 29, 2022

(54) MAGNOLIA BARK EXTRACT AS A HYDROPHOBIC LIGAND FOR PREFERENTIAL REMOVAL OF GRAM NEGATIVE BACTERIA FROM THE ORAL CAVITY

(71) Applicant: WM. WRIGLEY JR. COMPANY, Chicago, IL (US)

(72) Inventors: Henk J. Busscher, Groningen (NL); Michael W. Dodds, LaGrange Park, IL (US); Amarnath Maitra, Glen Ellyn, IL (US); Stefan Wessel, Groningen (NL); Henny C. Van Der Mei, Groningen (NL)

(73) Assignee: WM. WRIGLEY JR. COMPANY, Chicago, IL (US)

(*) Notice: Subject to any disclaimer, the term of this patent is extended or adjusted under 35 U.S.C. 154(b) by 0 days.

(21) Appl. No.: 15/743,689

(22) PCT Filed: Jul. 14, 2016

(86) PCT No.: PCT/US2016/042296
§ 371 (c)(1),
(2) Date: Jan. 11, 2018

(87) PCT Pub. No.: WO2017/011665
PCT Pub. Date: Jan. 19, 2017

(65) Prior Publication Data
US 2018/0200180 A1    Jul. 19, 2018

Related U.S. Application Data

(60) Provisional application No. 62/192,282, filed on Jul. 14, 2015.

(51) Int. Cl.
*A61K 8/9789* (2017.01)
*A61Q 11/00* (2006.01)
*A61K 36/575* (2006.01)
*A61K 8/31* (2006.01)
*A61K 8/34* (2006.01)
*A61K 8/36* (2006.01)

(52) U.S. Cl.
CPC ............ *A61K 8/9789* (2017.08); *A61K 8/31* (2013.01); *A61K 8/347* (2013.01); *A61K 8/361* (2013.01); *A61K 36/575* (2013.01); *A61Q 11/00* (2013.01); *A61K 2800/592* (2013.01)

(58) Field of Classification Search
None
See application file for complete search history.

(56) References Cited

U.S. PATENT DOCUMENTS

| 4,525,342 | A  | * | 6/1985  | Weiss  | A61K 8/67 222/129.4 |
| 6,689,342 | B1 | * | 2/2004  | Pan    | A61K 8/35 424/435 |
| 6,723,304 | B2 | * | 4/2004  | Stier  | A61K 8/345 424/48 |
| 10,653,140 | B2 | * | 5/2020  | Davies | A01N 37/02 |
| 2004/0022817 | A1 | * | 2/2004 | Tardi | A61K 9/0019 424/400 |
| 2006/0013779 | A1 |   | 1/2006 | Dodds | |
| 2006/0275222 | A1 |   | 12/2006 | Dodds et al. | |
| 2007/0134168 | A1 |   | 6/2007 | Dodds | |
| 2007/0134171 | A1 | * | 6/2007 | Dodds | A61K 8/02 424/58 |
| 2012/0294812 | A1 | * | 11/2012 | Fei | A61K 8/347 424/49 |
| 2018/0200180 | A1 |   | 7/2018 | Busscher | |

FOREIGN PATENT DOCUMENTS

| JP | 4440622 B2 * | 3/2010 | |
| WO | 200170184 A2 | 9/2001 | |
| WO | 2004004650 A2 | 1/2004 | |
| WO | WO2007064505 A1 | 6/2007 | |
| WO | WO-2007064519 A1 * | 6/2007 | ............ A61K 8/02 |
| WO | WO2007126651 A3 | 3/2008 | |
| WO | WO2017011665 A1 | 1/2017 | |

OTHER PUBLICATIONS

Mizrahi B, Citrus oil and MgCl2 as antibacterial and anti-inflammatory agents, J Periodontol, 2006, 77, 963-968 (Year: 2006).*
Lee et al., "Lycopene-induced hydroxyl radical causes oxidative DNA damage in *Escherichia coli*," J. Microbiol. Biotechnol., 2014, 24(9):1232-1237.
Prajapati et al., "A Comparative Evaluation of Mono-, Di- and Triglyceride of Medium Chain Fatty Acids by Lipid/Surfactant/Water Phase Diagram, Solubility Determination and Dispersion Testing for Application in Pharmaceutical Dosage Form Development," Pharm Res (2012) 29:285-305.
European Patent Office, Communication of a notice of opposition, EP 3322487 (filed Jul. 14, 2016), dated Oct. 26, 2021, 17 pages.
Amelia et al., GC-MS analysis o fclove (*Syzygium aromaticum*) bud essential oil from Java and Manado, AIP Conference Proceedings 1862, 030082 (published online: Jul. 10, 2017), 10 pages.
Abdelwahab et al., "Chemical composition and antioxidant properties of the essential oil of Cinnamomum altissimum Kosterm. (*Lauraceae*)", Arabian Journal of Chemistry, (2017) 10, pp. 131-135.
Greenberg et al., "Compressed Mints and Chewing Gum Containing Magnolia Bark Extract Are Effective against Bacteria Responsible for Oral Malodor", J. Agric Food Chem. 2007, 55, pp. 9465-9469.
Schmidt et al., "Chemical Composition, Olfactory Evaluation and Antioxidant Effects of Essential Oil from Mentha x piperita", NPC-Natural Product Communications, Feb. 2009, vol. 4, No. 8, pp. 1107-1112.

(Continued)

*Primary Examiner* — Celeste A Roney (57) ABSTRACT

The present disclosure relates generally to oral compositions and methods for freshening breath and oral cleansing, and more particularly, to oral compositions comprising a combination of an extract of *magnolia* and a hydrocarbon. The oral compositions are useful for improving oral health, including freshening breath and reducing the adherence of plaque to teeth.

6 Claims, 5 Drawing Sheets

(56) References Cited

OTHER PUBLICATIONS

Dahham et al., "The Anticancer, Antioxidant and Antimicrobial Properties of the Sesquiterpene β-Caryophyllene from the Essential Oil of Aquilaria crassna", Molecules, 2015, 20, pp. 11808-11829.
Determination of myrcene, limonene and menthol by means of GC-MS-HS, by Politecnico di Milano, dated Jul. 21, 2021, 12 pages.
Affidavit executed by Andrea Farrica, Oct. 4, 2021, 1 page.
Perfetti Van Melle Benelux BV Invoice #91296862, dated Mar. 3, 2015, 1 page.
Perfetti Van Melle Benelux BV Invoice #90749898, dated May 18, 2015, 1 page.
Innova Markets Insights, Extracts from www.innovadatabase.com, obtained 2021, 5 pages.

\* cited by examiner

MAGNOLIA BARK EXTRACT AS A HYDROPHOBIC LIGAND FOR PREFERENTIAL REMOVAL OF GRAM NEGATIVE BACTERIA FROM THE ORAL CAVITY

CROSS-REFERENCE TO RELATED APPLICATIONS

This application claims the benefit of U.S. Provisional Application Ser. No. 62/192,282, filed Jul. 14, 2015, which is herein incorporated by reference in its entirety.

BACKGROUND OF THE DISCLOSURE

The present disclosure relates generally to oral compositions and methods for freshening breath and oral cleansing, and more particularly, to oral compositions comprising a combination of an extract of *magnolia* and a hydrocarbon. The oral compositions are useful for improving oral health, including freshening breath and reducing the adherence of plaque to teeth.

The oral cavity is comprised of more than 700 bacterial species (Aas, et al., "Defining the normal bacterial flora of the oral cavity," J. Clin. Microbiol., 2005, Vol. 43(11), pp. 5721-32) that live together in symbiosis at times of good oral health (Zarco, et al., "The oral microbiome in health and disease and the potential impact on personalized dental medicine," Oral. Dis., 2012, Vol. 18(2), pp. 109-20). An ecological shift in the oral microbiome, due to various extrinsic or intrinsic stimuli, can result in an abundance of certain pathogenic bacterial strains and cause oral disease, such as caries, gingivitis, and/or halitosis. The key to maintenance of oral health is maintaining the symbiotic nature of the oral microbiome and preventing overgrowth of pathogenic species within the oral biofilm. This is largely achieved by regular oral hygiene, such as toothbrushing, which mechanically removes the oral biofilm. Dental floss, toothpicks, mouthrinses, and chewing gum have also been promoted as adjuncts to regular oral hygiene (see Imfeld, T., "Chewing gum—facts and fiction: A review of gum-chewing and oral health," Crit. Rev. Oral Biol. Med., 1999, Vol. 10(3), pp. 405-19; Crocombe, et al. "Is self interdental cleaning associated with dental plaque levels, dental calculus, gingivitis and periodontal disease?" J. Periodontal Res., 2012, Vol. 47(1), pp. 188-97).

Nonetheless, maintaining oral health is difficult, and other ways of influencing the oral microbiome have been explored, for instance, by topical administration of active ingredients. As early as 1967, it was demonstrated that the microbiome of the oral biofilm could be shifted towards a composition of solely Gram negative bacteria by rinsing with vancomycin (Loe, et al., "Experimental Gingivitis" in Man. J. Periodontol., 1967, Vol. 36, pp. 177-87). Another study has shown that a mouth rinse containing essential oils, in combination with the use of a toothpaste with triclosan, was also able to change the composition of the oral biofilm (Jongsma, et al., "In vivo biofilm formation on stainless steel bonded retainers during different oral health-care regimens," Int. J. Oral Sci., 2015, Vol. 7, pp. 42-48). In this study, the shift in microbiome was attributed to changes in the cell surface hydrophobicity of oral bacteria due to the non-polar triclosan facilitating adhesion of specific bacteria to the essential oils in the mouth rinse, and subsequent removal from the oral cavity. Previously, amoxicillin, penicillin, metronidazole and cetylpyridinium chloride were also suggested to be able to change cell surface hydrophobicity of specific strains of oral bacteria at low concentrations (see Goldberg, et al., "Effect of cetylpyridinium chloride on microbial adhesion to hexadecane and polystyrene," Appl. Environ. Microbiol., 1990, Vol. 56(6), pp. 1678-82; Lee, et al., "Subinhibitory Concentrations of Antibiotics Affect Cell-surface Hydrophobicity and Morphology of *Porphyromonas gingivalis* and *Fusobacterium nucleatum*," 81st General Session of the International Association for Dental Research—Jun. 25-28 2003, Abstract #2157).

There is thus a need for other oral compositions that can be used to facilitate removal of bacteria from the oral cavity. It would be particularly advantageous to have an oral composition that promotes oral health, and more specifically, that preferentially targets oral bacteria responsible for oral health issues, such as plaque formation and halitosis.

SUMMARY OF THE DISCLOSURE

The present disclosure relates to oral compositions and methods for freshening breath and oral cleansing. In particular, the disclosure is directed to oral compositions comprising a *magnolia* extract and a hydrocarbon. The *magnolia* extract present in the oral composition acts as a hydrophobic ligand that enhances the cell surface hydrophobicity of certain oral bacteria, thus facilitating the adherence of these bacteria to the hydrocarbon, and their subsequent removal from the oral cavity.

Thus, in one aspect, the present disclosure is directed to an oral composition for freshening breath. The oral composition comprises a *magnolia* extract and a hydrocarbon, wherein the hydrocarbon is selected from the group consisting of hexadecane, a terpene, and combinations thereof.

In another aspect, the present disclosure is directed to an oral composition for freshening breath, the oral composition comprising a *magnolia* extract and from about 0.001% to about 10.0% by weight of a hydrocarbon, wherein the hydrocarbon is selected from the group consisting of fatty acids and esters.

In another aspect, the present disclosure is directed to an oral composition for freshening breath, the oral composition comprising magnolol and from about 0.001% to about 10.0% by weight of a hydrocarbon, wherein the hydrocarbon is selected from the group consisting of hexadecane, a terpene, fatty acids, esters, and combinations thereof.

In still another aspect, the present disclosure is directed to a method for reducing the adherence of plaque to teeth. The method comprises contacting the teeth with an oral composition of the present disclosure.

In yet another aspect, the present disclosure is directed to a method for freshening the breath of a mammalian subject, the method comprising contacting a composition of the present disclosure with the oral cavity of the subject.

DETAILED DESCRIPTION OF THE DISCLOSURE

The present disclosure relates to oral compositions and methods for freshening breath and oral cleansing. More particularly, the disclosure relates to oral compositions comprising an extract of *magnolia* and a hydrocarbon. The oral compositions are useful for improving oral health, including freshening breath and reducing the adherence of plaque to teeth.

Without wishing to be bound to any particular theory, it is believed that the extract of *magnolia* present in the oral composition acts as a hydrophobic ligand that enhances the cell surface hydrophobicity of certain oral bacteria, thus facilitating the adherence of these bacteria to the hydrocarbon, and their subsequent removal from the oral cavity (e.g., by swallowing of the hydrocarbon and/or being absorbed into an oral composition such as chewing gum).

Surprisingly, it has been discovered that *magnolia* extract shows a greater enhancement of cell surface hydrophobicity of Gram negative oral bacteria, as compared to Gram positive bacteria. The compositions of the present disclosure can thus be used to preferentially remove Gram negative bacteria from the oral cavity. Since Gram negative bacteria are known to contribute to halitosis, the compositions of the present invention can be used to freshen breath.

Thus, in another aspect, the present disclosure is directed to a method for freshening the breath of a mammalian subject, comprising contacting a composition of the present disclosure with the oral cavity of the subject. The subject may be human, or a non-human animal.

In another aspect, the oral compositions of the present disclosure may be used to reduce the adherence of plaque to teeth. In particular, plaque (also referred to as "dental plaque") is a biofilm or mass of bacteria that grows on surfaces within the oral cavity. Plaque may lead to various oral diseases such as caries and periodontal diseases. *Streptococcus mutans* (a Gram-positive, facultatively anaerobic bacteria) is one of the primary components of plaque and causes of dental caries. It has now been discovered that *magnolia* extract produces a relatively low, but significant, increase in cell surface hydrophobicity of the Gram positive, plaque forming bacteria *S. mutans*.

Thus, in another aspect, the present disclosure is directed to a method for reducing the adherence of plaque to teeth, comprising contacting the teeth with an oral composition of the present disclosure. The teeth may be human or non-human mammalian teeth (e.g., when the composition is an animal treat).

Cell Surface Hydrophobicity

The change in cell surface hydrophobicity of Gram negative and Gram positive bacteria resulting from contact with the *magnolia* extract can be measured using the kinetic Microbial Adhesion To Hydrocarbon (MATH) test. The kinetic MATH test has been previously described by Lichtenberg, et al. ("A kinetic approach to bacterial adherence to hydrocarbons," *J. Microbiol. Methods*, 1985, Vol. 4, pp. 141-6), and is discussed in detail in the examples.

Briefly, the optical density at 600 nm of a suspension of bacteria in saliva buffer and *magnolia* extract is measured ($A_0$) using a spectrophotometer relative to saliva buffer without bacterial suspension and *magnolia* extract. Subsequently, a hydrocarbon (e.g., hexadecane, n-dodecane, or octane) is added to the suspension, which is briefly mixed with a vortex mixer. The suspension is allowed to settle for phase separation, and the optical density of the aqueous phase is measured again ($A_t$). The removal of bacteria from the saliva buffer to the hydrocarbon (e.g., hexadecane, n-dodecane, or octane) is expressed as log ($A_t/A_0 \times 100$), and plotted as a function of the vortexing time. The initial removal rate ($R_0$) represents the bacterial removal rate per minute from the suspension to the hydrocarbon, and is a measure for cell surface hydrophobicity. The initial removal rate ($R_0$) is calculated as the slope of the tangent of the curve.

Figure 3A:
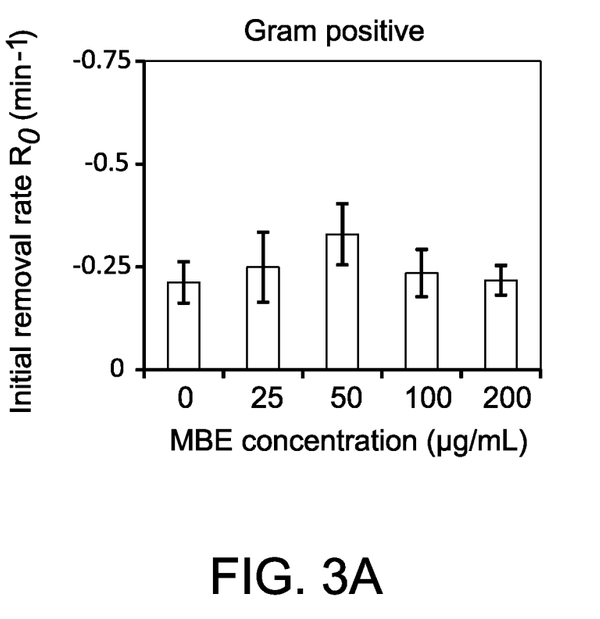
FIGS. 3A and 3B are charts depicting the cell surface hydrophobicity, expressed as removal rate per min by hexadecane ($R_0$ ($min^{-1}$)), averaged for all of the Gram positive (FIG. 3A) and Gram negative (FIG. 3B) bacteria listed in FIG. 2. The removal rate of Gram negative bacteria increased with increasing concentrations of MBE. Error bars denote standard error of the mean.
Figure 3B:
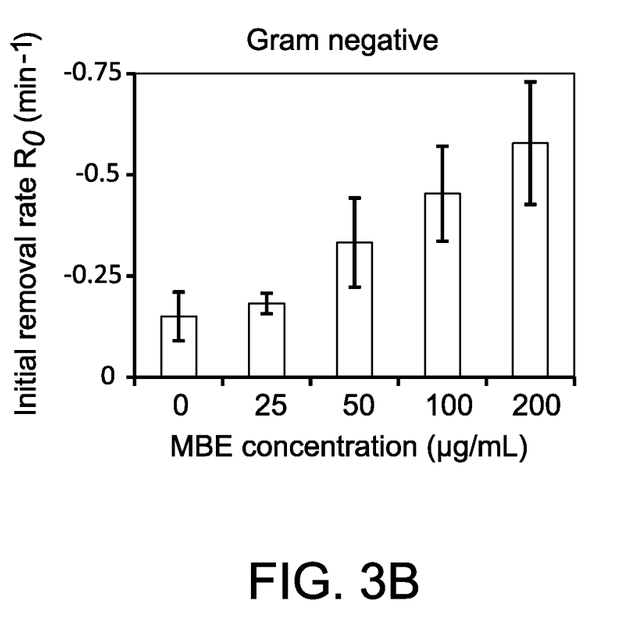

As demonstrated in the examples, and illustrated in FIGS. 3A and 3B, it has now been discovered that the average removal rate for Gram negative bacteria strains significantly increases with increasing concentrations of *magnolia* extract, while the average removal rate of Gram positive strains was not influenced by the presence of *magnolia* extract. There was also a low, but significant, increase in removal rate with increasing concentrations of *magnolia* extract for *S. mutans*.

*Magnolia* Bark Extract

The compositions of the present disclosure comprise extract of *magnolia* (also referred to herein "*magnolia* extract," "*magnolia* bark extract," or "MBE"). As referred to herein, such an "extract" of *magnolia* is an extract from dried cortex, or bark, of a plant from the Magnoliaceae family, such as *Magnolia officinalis*, ("*magnolia*") or a synthetic or semi-synthetic equivalent of such an extract or an active component or compound thereof. Typically, extracts of *Magnolia* Cortex (the bark of *Magnolia officinalis*) contain hydrophobic compounds including magnolol, honokiol, tetrahydromagnolol, and tetrahydrohonokiol. Any plant from the Magnoliaceae family is suitable for the present invention and may be used in alternate embodiments, preferably such that the extract comprises an effective concentration of a compound selected from the group consisting of magnolol, honokiol, tetrahydromagnolol, tetrahydrohonokiol, and combinations thereof, and preferably an effective concentration of magnolol and/or honokiol. As used herein, an "effective concentration" of *magnolia* extract (or an active(s) therein) is a concentration that results in an increase in the initial removal rate of a bacteria as measured by the kinetic MATH test.

As used herein, "extracting" or "extraction" of a solid or liquid material means contacting the material with an appropriate solvent to remove the substance(s) desired to be extracted from the material. Where the material is solid, it is preferably dried and crushed or ground prior to contacting it with the solvent. Such an extraction may be carried out by conventional means known to one of skill in the art, for example, by using an extraction apparatus, such as a Soxhlet apparatus, which retains the solid material in a holder and allows the solvent to flow through the material; or by blending the solvent and material together and then separating the liquid and solid phases or two immiscible liquid phases, such as by filtration or by settling and decanting.

In one embodiment, *magnolia* extract is made from dried *Magnolia* plant bark and can be prepared by extracting the bark using an appropriate solvent. Solvents include compatible liquids such as hydrocarbons and substituted hydrocarbons containing up to about 20 carbon atoms, such as alkanes, alcohols, halogenated alkanes, ethers, and the like, and specifically including methanol, ethanol, methylene chloride, hexane, cyclohexane, pentane, petroleum ether, chloroform, ethylene dichloride, and hydrofluoroalkanes, such as 1, 1, 1, 2-tetrafluoroethane (HFA-13A). Generally, one part of plant tissue (dry basis) is extracted with about 5 to about 50 parts, preferably about 15 parts to about 30 parts of solvent using an extraction apparatus where the solvent is contacted with the bark to obtain a concentrated paste which is then subjected to one or more additional extraction steps with different solvents to further concentrate the originally obtained paste over an extended period of time, preferably about 6 to 48 hours, more preferably for about one day. In one simplified method of extraction, the dried, crushed *Magnolia* bark in the form of a powder is contacted with a hydrofluoroalkane (such as, 1,1,1,2-tetrafluoroethane (HFA-13A)) to form a concentrated final extraction yielding an extract containing about 5 to about 50% honokiol and about 5 to about 50% magnolol.

In preferred embodiments, the natural extract active ingredients used in oral compositions are reproducible, stable, and have microbiological safety. In one embodiment of the present invention, the *magnolia* extract is isolated by supercritical fluid extraction (SFE) using carbon dioxide ($CO_2$). Supercritical fluids are gases with properties between that of a "normal" phase of gas and liquid. Pressure variations control the properties of the supercritical fluids, which can range from more gas-like behavior to more liquid-like behavior, depending on the application. Supercritical fluids use a solvent that is readily available, inexpensive, and environmentally safe (such as $CO_2$). Carbon dioxide is non-toxic, non-explosive, readily available and easily removed from the extracted products. Process temperatures for SFE are generally low to moderate. Thus, SFE produces nearly solvent-free products, and further avoid any potential deterioration reactions.

Natural contaminants which may be potentially present in other extraction methodologies are generally absent in the SFE extracted product. For example, compounds such as aristocholic acid and alkaloids, such as magnocurine and tubocurarine, are kept at low concentrations (for example, generally less than 0.0002 percent). Thus, in the embodiment where the *magnolia* is extracted by SFE, the extract is substantially free from chemical alterations brought about by heat and water, from solvent residues, and other artifacts.

Further, certain SFE *magnolia* extracts are cosmetically acceptable. Certain methods of *magnolia* extraction produce a dark brown product that is difficult to formulate in an oral composition, due to the dark color, even at low concentrations. In certain embodiments, SFE extraction produces a much lighter color of *magnolia* extract (a light beige product) that is particularly suitable for aesthetically pleasing oral composition formulations.

As noted above, the *magnolia* extract is believed to act as a hydrophobic ligand to alter the cell surface hydrophobicity of the bacteria. In various embodiments, it is preferred that the active hydrophobic ingredient in the *magnolia* extract comprises either magnolol, honokiol, or both. Magnolol and honokiol are non-ionic hydroxybiphenyl compounds, the structures of which are believed to be as follows:

Honokiol

Magnolol

Additionally, tetrahydromagnolol and tetrahydrohonokiol are hydrogenated analogs of magnolol and honokiol often found in relatively small concentrations in the extracts of *magnolia*, and as such may be included in the composition.

Thus, as will be described in greater detail below, in various embodiments of the present invention, the *magnolia* extract comprises one or more hydrophobic compounds: magnolol, honokiol, tertrahydromagnolol, tetrahydrohonokiol, and mixtures thereof, which are used in combination with a hydrocarbon to selectively remove Gram negative bacteria (associated with halitosis) present in the oral cavity.

*Magnolia* extracts useful in this invention are commercially available. One such extract is obtained by supercritical carbon dioxide extraction, comprising a total content of magnolol higher than 90%.

In various embodiments, *magnolia* extract of the present invention comprises magnolol, honokiol, or both in an amount of about 2% to about 99% by weight. In other embodiments, *magnolia* extract comprises magnolol, honokiol, or both in an amount greater than 50% by weight. In one embodiment of the present invention, the magnolol is present in an amount greater than 50% by weight, greater than 70% by weight or most preferably, greater than 90% by weight. In another embodiment, honokiol is present in an amount less than 50% by weight, more preferably in an amount less than 30% by weight, or most preferably, less than 10% by weight.

In some embodiments, *magnolia* extract is present in the oral composition in an amount of about 0.001 to about 5% by weight. In one embodiment, *magnolia* extract is present in the oral composition in an amount of about 0.001 to about 3% by weight. In other embodiments, the *magnolia* extract is present at less than 1% by weight, for example the extract is present in an amount of about 0.01 to about 1% by weight, or about 0.001 to about 0.5% by weight. In one embodiment, the *magnolia* extract is present at amounts up to 0.2% by weight. In one preferred embodiment, the *magnolia* extract is present in the oral composition at a concentration of about 0.02% by weight. More preferably, the concentration of

*magnolia* extract is below a level which produces a discoloration on teeth and most preferably below a level which produces an objectionable taste.

Preferably, the amount of hydrocarbon in the oral compositions will exceed the amount of *magnolia* extract in the composition. Thus, the weight ratio of *magnolia* extract to hydrocarbon in the oral compositions will preferably be 1 to greater than 1.

In some embodiments, the oral compositions of the present disclosure may comprise magnolol as the active hydrophobic ingredient. The magnolol may be from any suitable source. For example, the magnolol may be included in the compositions as part of a *magnolia* extract, or alternately may be isolated from other components of the *magnolia* extract prior to inclusion in the oral compositions. The magnolol may be present in the oral compositions in an amount of about 0.001 to about 5% by weight. In some embodiments, the magnolol may be present in the oral composition in an amount of about 0.001 to about 3% by weight, or about 0.01 to about 1% by weight, or about 0.001 to about 0.5% by weight.

Hydrocarbons

In addition to the *magnolia* extract, the oral compositions of the disclosure comprise a hydrocarbon. As used herein, the term "hydrocarbon" includes both unsubstituted hydrocarbons and hydrocarbon derivatives, such as substituted hydrocarbons. In some embodiments, the hydrocarbons are food grade unsaturated hydrocarbons, such as hexadecane and/or terpenes. Food grade hydrocarbons include hydrocarbons that are suitable for use as food additives, and that may be designated by the United States FDA as generally regarded as safe (GRAS) or FEMA GRAS (Intl. Flavor Manuf Assoc.). Suitable terpenes include monoterpenes (e.g., limonene, myrcene, etc.), diterpenes, tetraterpenes (e.g., lycopene), sesquiterpene, and combinations thereof. In some embodiments, the hydrocarbons are hydrocarbon derivatives, such as fatty acids, esters, and combinations thereof. Non-limiting examples of suitable fatty acids include $C_{10}$ to $C_{18}$ fatty acids, such as stearic, palmitic, oleic and linoleic acids. Non-limiting examples of suitable esters include triglycerides, such as NEOBEE® medium chain triglycerides (available from Stepan Company), tri-acetin, glucose stearate, magnesium stearate, and combinations thereof. Suitable NEOBEE® medium chain triglycerides include NEOBEE® 895 (a caprylic triglyceride), NEOBEE® 1053 or NEOBEE® M-5 (caprylic/capric triglycerides), or NEOBEE® M-20 (propylene glycol di(caprylate/caprate)).

The hydrocarbon is present in the oral composition in an amount of about 0.001 to about 10% by weight. In some embodiments, the hydrocarbon is present in the oral composition in an amount of about 0.001 to about 5.0% by weight, or about 0.001 to about 2.0% by weight. In a preferred embodiment, the hydrocarbon is present in the oral composition in an amount of about 0.5 to about 2.0% by weight. In one embodiment, the hydrocarbon is present in the oral composition in an amount of about 2.0% by weight. In other embodiments, the hydrocarbon is present in amounts less than 1% by weight, for example the hydrocarbon may be present in the oral composition in an amount of from about 0.01 to about 1% by weight. Preferably, the hydrocarbon is present in the oral compositions in a higher weight amount than the *magnolia* extract.

Oral Composition

The oral compositions of the present disclosure comprising *magnolia* extract and a hydrocarbon are in the form of a food-acceptable or food contact acceptable material or carrier in which *magnolia* extract and hydrocarbon may be incorporated or dispersed without adverse effect. The oral composition may be a water-soluble solid or chewable solid such as chewing gums (e.g., tablet gums, pellet or dragee gums, stick gums, compressed gums, co-extruded layered gums, bubble gums, etc.), confections (e.g., candies, chocolates, gels, confectionery pastes, etc.), or orally soluble tablets, beads, lozenges, or capsules. In some embodiments, the composition is a confectionery composition in the form of a coating, shell, film, syrup, or suspension. In other embodiments, *magnolia* extract and a hydrocarbon, are "admixed" with or added to the complete chewing gum or confectionary composition. As used herein, "admixing," refers to the process where the *magnolia* extract and a hydrocarbon are mixed with or added to the completed composition or mixed with some or all of the components of the composition during product formation or some combination of these steps. When used in the context of admixing, the term "product" refers to the product or any of its components. This admixing step can include a process selected from the step of adding the *magnolia* extract and a hydrocarbon to the composition, spraying the *magnolia* extract and a hydrocarbon on the product, coating the *magnolia* extract and a hydrocarbon on the product, suspending the *magnolia* extract and a hydrocarbon in the product, painting the *magnolia* extract and a hydrocarbon on the product, pasting the *magnolia* extract and a hydrocarbon on the product, encapsulating the product with the *magnolia* extract and a hydrocarbon, mixing the *magnolia* extract and a hydrocarbon with the product and any combination thereof. The *magnolia* extract and the hydrocarbon may be admixed together or separately, and can be a liquid, dry powder, spray, paste, suspension, or any combination thereof.

Such delivery systems are well known to one of skill in the art, and preparation generally entails stirring the *magnolia* extract and hydrocarbon into a warm base with flavor and non-cariogenic sweeteners. Other suitable oral compositions include mouth rinses and dentifrices (such as a paste or powder). In some embodiments, the oral composition may be suitable for use by non-human mammals, and may be, for example, an animal treat biscuit.

The materials included in the oral compositions encompassed herein are intended to be non-toxic. For the purpose of this disclosure, the term "non-toxic" is intended to conform with accepted and established definitions of safety, such as described by the designation "generally accepted as safe" by the Food and Drug Administration. Also, encompassed in this definition are those compounds that have been added to food for some time and which are recognized as safe under conditions of their intended use.

Chewing Gums

In one embodiment, the oral composition of the present disclosure is a chewing gum. The chewing gum may include the *magnolia* extract and hydrocarbon in any of the amounts set forth herein. In one particular embodiment, the chewing gum may comprise up to about 0.2% by weight of *magnolia* extract and about 2.0% by weight of hydrocarbon. Chewing gum products of the present disclosure may be made using a variety of different compositions that are typically used in chewing gum compositions. Suitable physical forms include sticks, tabs, dragees, chicklets, batons, and the like. Although exact ingredients for each product form will vary from product to product, the specific techniques will be known by one skilled in the art. In general, a chewing gum composition typically contains a chewable gum base portion which is essentially water-insoluble, and a water-soluble bulk portion which includes water soluble bulking agents and other water soluble components as well as flavors and perhaps other active ingredients which are typically water-insoluble. The water-soluble portion dissipates with a portion of the flavor (and other water insoluble actives, if present) over a period of time during chewing. The gum base portion is retained in the mouth throughout the chew.

The chewing gum may comprise between approximately 5% to about 95% by weight gum base. Typically, the insoluble gum base may comprise between approximately 10% and about 50% by weight of the gum, or from approximately 20% to about 40% by weight of the gum. The present disclosure contemplates employing any commercially acceptable gum base.

The insoluble gum base generally comprises elastomers, elastomer solvents, plasticizers, waxes, emulsifiers, and inorganic fillers. Plastic polymers, such as polyvinyl acetate, which behave somewhat as plasticizers, are also included. Other plastic polymers that may be used include polyvinyl laurate, polyvinyl alcohol, and polyvinyl pyrrolidone. Gum base typically comprises 20 to 40% by weight of the overall chewing gum composition. However, in less common formulations it may comprise as low as 5% or as high as 95% by weight.

Synthetic elastomers may include, but are not limited to, polyisobutylene (e.g. having a weight average molecular weight of about 10,000 to about 95,000), butyl rubber (isobutylene-isoprene copolymer), styrene copolymers (having for example a styrene-butadiene ratio of about 1:3 to about 3:1), polyisoprene, polyethylene, vinyl acetate-vinyl laurate copolymer (having for example a vinyl laurate content of about 5% to about 50% by weight of the copolymer), and combinations thereof.

Natural elastomers may include for example natural rubbers such as smoke or liquid latex and guayule, as well as natural gums such as chicle, jelutong, lechi caspi, perillo, sorva, massaranduba balata, massaranduba chocolate, nispero, rosindinha, gutta hang kang and mixtures thereof. Preferred elastomers will depend on, for example, whether the chewing gum in which the base is used is adhesive or conventional, synthetic or natural, bubble gum or regular gum. Elastomers provide the rubbery texture which is characteristic of chewing gum. Elastomers typically make up 5 to 25% by weight of the gum base.

Elastomer solvents which are sometimes referred to as elastomer plasticizers, include but are not limited to natural rosin esters such as glycerol esters, or partially hydrogenated rosin, glycerol esters of polymerized rosin, glycerol esters of partially dimerized rosin, glycerol esters of rosin, pentaerythritol esters of partially hydrogenated rosin, methyl and partially hydrogenated methyl esters of rosin, pentaerythritol esters of rosin, synthetics such as terpene resins, polylimonene and other polyterpenes and/or any suitable combination of the forgoing. Elastomer solvents are typically employed at levels of 5 to 30% by weight of the gum base.

Gum base plasticizers are sometimes referred to as softeners (but are not to be confused with water soluble softeners used in the water soluble portion of the gum). Typically, these include fats and oils as well as waxes. Fats and oils are typically vegetable oils which are usually partially or fully hydrogenated to increase their melting point. Vegetable oils suitable for such use include oils of cottonseed, soybean, palm (including palm kernal), coconut, shea, castor, peanut, corn, rapeseed, canola, sunflower, cocoa and others. Less commonly used are animal fats such as milk fat, tallow and lard. Structured fats, which are essentially synthetically compounded glycerol esters (triglycerides) of fatty acids of varying chain lengths, offer an ability to carefully adjust the softening profile by use of short and medium chain fatty acids which are less commonly found in nature. Commonly employed waxes include paraffin, microcrystalline and natural waxes such as beeswax and carnauba. Microcrystalline waxes, especially those with a high degree of crystallinity, may be considered bodying agents or textural modifiers. Plasticizers are typically employed at a level of 5 to 40% by weight of the gum base.

Plastic polymers, such as polyvinyl acetate, which behave somewhat as plasticizers, are also commonly used. Other plastic polymers that may be used include polyvinyl laurate, polyvinyl alcohol, and polyvinyl pyrrolidone. Most gum bases incorporate polyvinyl acetate at a level of 5 to 40% by weight of the gum base.

The gum base typically also includes a filler component. The filler component is typically an inorganic powder such as calcium carbonate, ground limestone, magnesium carbonate, talc, silicate types such as aluminum and magnesium silicate, dicalcium phosphate, tricalcium phosphate, cellulose polymers, such as wood, combinations thereof and the like. The filler may constitute from 5% to about 50% by weight of the gum base. Occasionally, a portion of the filler may be added to the chewing gum mixture separately from the gum base.

Emulsifiers, which may also have plasticizing properties, assist in homogenizing and compatibilizing the different base components. Commonly used emulsifiers include mono- and diglycerides such as glycerol monostearate, lecithin, glycerol triacetate, glycerol monostearate, acetylated monoglycerides, fatty acids and combinations thereof. Emulsifiers are commonly used at a level of 1 to 10% by weight of the gum base.

Gum bases commonly contain optional additives such as antioxidants and colors which serve their normal functions. Less commonly, flavors and sweeteners may be added to the gum base. These additives, if used, are typically employed at levels of about 1% or less by weight of the gum base.

The water-soluble portion of the chewing gum may comprise softeners, sweeteners, flavoring agents, and combinations thereof as well as other optional ingredients. For example, the majority of the water soluble portion of the chewing gum will typically comprise a water-soluble, powdered carbohydrate which serves as a bulking agent. In sugar gums, this most often is sucrose although other sugars such as fructose, erythrose, dextrose (glucose), levulose, tagatose, galactose, trehalose, corn syrup solids and the like, alone or in any combination may also be used.

Generally, sugarless chewing gums will employ sugar alcohols (also called alditols, polyols or polyhydric alcohols) as bulking agents due to their benefits of low cariogenicity, reduced caloric content and reduced glycemic values. Such sugar alcohols include sorbitol, mannitol, xylitol, hydrogenated isomaltulose, maltitol, erythritol, hydrogenated starch hydrolysate solids, and the like, alone or in any combination. Longer chain saccharides such as polydextrose and fructo-oligosaccharides are sometimes employed for their reduced caloric properties and other health benefits. The bulking agents typically comprise approximately 5% to about 95% by weight of the gum composition.

Softeners are added to the chewing gum in order to optimize the chewability and mouth feel of the gum. Softeners, also known in the art as plasticizers or plasticizing agents, generally constitute between approximately 0.5% to about 15% by weight of the chewing gum. These include glycerin, propylene glycol and aqueous sweetener solutions (syrups). Examples of syrups include corn syrups and (generically) glucose syrups which are usually prepared from hydrolyzed starch. For sugarless products, the starch hydrolysate may be hydrogenated to produce an ingredient known as hydrogenated starch hydrolysate syrups or maltitol syrups. These HSH syrups have largely replaced sorbitol solutions previously used in sugarless gums because they also function as binders to improve the flexibility and other physical properties of the gum. Softeners are also often used to control the humectancy (water absorbing properties) of the product.

It is often desirable to combine aqueous softeners with glycerin or propylene glycol. One way to accomplish this is through the use of co-evaporated syrups such as those disclosed in U.S. Pat. No. 4,671,961, which is incorporated herein by reference. These syrups provide the benefits of both types of softeners in a single, pumpable liquid with minimal water content.

An emulsifier is sometimes added to the gum to improve the consistency and stability of the gum product. They may also contribute to product softness. Lecithin is the most commonly employed emulsifier, although nonionic emulsifiers such as polyoxyethylene sorbitan fatty acid esters and partial esters of common fatty acids (lauric, palmitic, stearic and oleic acid hexitol anhydrides (hexitans and hexides) derived from sorbitol may also be used. When used, emulsifiers typically comprised 0.5 to 2% by weight of the chewing gum composition.

Suitable surface active agents include surface active agents, which can be salts of potassium, ammonium, or sodium. Sodium salts include anionic surface active agents, such as alkyl sulfates, including sodium lauryl sulfate, sodium laureth sulfate, and the like. Other sodium salts include sodium lauroyl sarcosinate, sodium brasslate, and the like. Suitable ammonium salts include betaine derivatives such as cocamidopropyl betaine, and the like.

In the case of sugarless gums, it is usually desirable to add high intensity sweeteners to compensate for the reduced sweetness resulting from substitution of sugar alcohols for the sucrose in sugar gums. More recently, the trend has been to also add high intensity sweeteners to sugar gums to boost and extend flavor and sweetness. High intensity sweeteners (which are sometimes called high potency or artificial sweeteners) may be defined as food acceptable chemicals which are at least twenty times sweeter than sucrose. Commonly used high intensity sweeteners include aspartame, sucralose, and acesulfame-K. Less common are saccharin, thaumatin, alitame, neotame, cyclamate, perilla derived sweeteners, stevia derived sweeteners, monatin, monellin and chalcones.

Usage levels for high intensity sweeteners may vary widely depending on the potency of the sweetener, local market preferences and the nature and level of other ingredients which might impart bitterness to the gum. Typical levels can range from about 0.01% to about 2% by weight, although some applications may dictate usage outside that range. These sweeteners may be combined together, or with non-high intensity sweeteners at varying levels to impart a sweetness synergy to the overall composition.

Flavors can be employed to impart a characteristic aroma and taste sensation to chewing gum products. Most flavors are water insoluble liquids but water soluble liquids and solids are also known. These flavors may be natural or artificial (synthetic) in origin. Often natural and artificial flavors are combined. It is also common to blend different flavors together in pleasing combinations. Although the range of flavors usable in chewing gums is nearly limitless, they commonly fall into several broad categories. Fruit flavors include lemon, orange, lime, grapefruit, tangerine, strawberry, apple, cherry, raspberry, blackberry, blueberry, banana, pineapple, cantaloupe, muskmelon, watermelon, grape, currant, mango, kiwi and many others as well as combinations. Mint flavors include spearmint, peppermint, wintergreen, basil, corn mint, menthol and others and mixtures thereof. Spice flavors include cinnamon, vanilla, clove, chocolate, nutmeg, coffee, licorice, eucalyptus, ginger, cardamom and many others. Also used are herbal and savory flavors such as popcorn, chili, corn chip and the like. Flavors are typically employed at levels of 0.1 to 4% by weight of the finished gum product. In recent years there has been a trend toward increasing flavor levels to provide higher flavor impact.

It is common to co-dry and encapsulate flavors with various carriers and/or diluents. For example, spray-dried flavors using gum Arabic, starch, cyclodextrin or other carriers are often used in chewing gum for protection, controlled release, control of product texture and easier handling as well as other reasons. When flavors are in such forms, it will often be necessary to increase the usage level to compensate for the presence of the carriers or diluents.

The chewing gum (along with any of the oral compositions) of the present disclosure may employ various sensates. Generally, sensates may be any compounds that cause a cooling, heating, warming, tingling or numbing, for example, to the mouth or skin. Cooling agents are trigeminal stimulants that impart a cool sensation to the mouth, throat and nasal passages. The most widely known cooling agent is menthol, although this is often considered a flavor due to its aroma properties and the fact that it is a natural component of peppermint oil. More often, the term cooling agent refers to other natural or synthetic chemicals used to impart a cooling sensation with minimal aroma. Commonly employed cooling agents include ethyl p-menthane carboxamide and other N-substituted p-menthane carboxamides, N,2,3-trimethyl-2-isopropyl-butanamide and other acyclic carboxamides, menthyl glutarate (Flavor Extract Manufacturing Association (FEMA 4006)), 3-1-menthoxypropane-1, 2-diol, isopulegol, menthyl succinate, menthol propylene glycol carbonate, menthol ethylene glycol carbonate, menthyl lactate, menthyl glutarate, menthone glyceryl ketal, p-menthane-1,8-diol, menthol glyceryl ether, N-tertbutyl-p-menthane-3-carboxamide, p-menthane-3-carboxylic acid glycerol ester, methyl-2-isopryl-bicyclo (2.2.1), heptane-2-carboxamide, menthol methyl ether and others and combinations thereof.

Cooling agents may be employed to enhance the cool taste of mint flavors or to add coolness to fruit and spice flavors. Cooling agents also provide the perception of breath freshening, which is the basis of the marketing of many chewing gums and confections.

Trigeminal stimulants other than cooling agents may be employed in the chewing gums of the present disclosure. These include warming agents such as capsaicin, capsicum oleoresin, red pepper oleoresin, black pepper oleoresin, piperine, ginger oleoresin, gingerol, shoagol, cinnamon oleoresin, cassia oleoresin, cinnamic aldehyde, eugenol, cyclic acetal of vanillin, menthol glycerin ether and unsaturated amides and tingling agents such as Jambu extract, vanillyl alkyl ethers such as vanillyl n-butyl ether, spilanthol, Echinacea extract and Northern Prickly Ash extract. Some of these components are also used as flavoring agents.

Chewing gum generally conveys oral care benefits. In addition to mechanical cleaning of the teeth provided by the chewing action, saliva stimulated by chewing, flavor and taste from the product conveys additional beneficial properties in reducing bad breath, neutralizing acid, and the like. Saliva also contains beneficial polypeptides and other components which may improve the oral environment. These include: antimicrobial proteins, such as lysozyme, lactoferrin, peroxidases, and histatins; inhibitors of spontaneous crystallization, such as statherin.

The chewing gums of the present disclosure can provide these benefits along with the benefits disclosed herein, and may also be used as vehicles for the delivery of specialized oral care agents. These may include antimicrobial compounds such as Cetylpyridinium Chloride (CPC), triclosan and chlorhexidine; anti-caries agents such as calcium and phosphate ions, plaque removal agents such as abrasives, surfactants and compound/ingredients; plaque neutralization agents such as ammonium salts, urea and other amines; anti-tartar/calculus agents such as soluble pyrophosphates salts; anti halitosis agents such as parsley oil and copper or zinc salts of gluconic acid, lactic acid, acetic acid or citric acid, and whitening agents such as peroxides; agents that may provide either local or systemic anti-inflammatory effects to limit gingivitis, such as COX-2 inhibitors; agents that may reduce dentinal hypersensitivity, such as potassium salts to inhibit nerve cell transmission, and calcium phosphate salts to block the dentinal tubules.

Certain flavors such as peppermint, methyl salicylate, thymol, eucalyptol, cinnamic aldehyde and clove oil (eugenol) may have antimicrobial properties which benefit the oral cavity. These flavors may be present primarily for flavoring purposes or may be added specifically for their antimicrobial properties.

Certain mineral agents may contribute to dental health, in addition to ones disclosed by the disclosure by combating demineralization and enhancing remineralization of teeth. Such ingredients include fluoride salts, dental abrasives and combinations thereof.

Teeth color modifying substances may be considered among the oral care actives useful. These substances are suitable for modifying the color of the teeth to satisfy the consumer such as those listed in the CTFA Cosmetic Ingredient Handbook, $3^{rd}$ Edition, Cosmetic and Fragrances Associations Inc., Wash. D.C. (1982), incorporated herein by reference. Specific examples include talc, mica, magnesium carbonate, magnesium silicate, aluminum magnesium carbonate, silica, titanium dioxide, zinc oxide, red iron oxide, brown iron oxide, yellow iron oxide, black iron oxide, ferric ammonium ferrocyanide, manganese violet, ultramarine, nylon powder, polyethylene powder and mixtures thereof.

The chewing gums of the present disclosure may be used to deliver biologically active agents to the chewer. Biologically active agents include vitamins, minerals, anti-oxidants, nutritional supplements, dietary supplements, functional food ingredients (e.g., probiotics, prebiotics, lycopene, phytosterols, stanol/sterol esters, omega-3 fatty acids, adenosine, lutein, zeaxanthin, grape seed extract, *Ginkgo biloba*, isothiocyanates and the like), OTC and prescription pharmaceuticals, vaccines, and nutritional supplements.

It may be desirable to take certain steps to increase or decrease the rate of the release of the agent or to ensure that at least a minimum quantity is released. Such measures as encapsulation, isolation of the active, measures to increase or decrease interaction with the water-insoluble portion of the gum and enteric coating of actives may be employed to that end.

In general, chewing gum is manufactured by sequentially adding the various chewing gum ingredients to a commercially available mixer known in the art. After the ingredients have been thoroughly mixed, the gum mass is discharged from the mixer and shaped into the desired form such as rolling sheets and cutting into sticks, extruding into chunks or casting into pellets, which are then coated or panned.

Generally, the ingredients are mixed by first melting the gum base and adding it to the running mixer. The base may also be melted in the mixer itself. Color or emulsifiers may also be added at this time. A softener such as glycerin may also be added at this time, along with syrup and a portion of the bulking agent. Further parts of the bulking agent are added to the mixer. Flavoring agents are typically added with the final portion of the bulking agent. Other optional ingredients are added to the batch in a typical fashion, well known to those of ordinary skill in the art.

The entire mixing procedure typically takes from five to fifteen minutes, but longer mixing times may sometimes be required. Those skilled in the art will recognize that many variations of the above described procedure may be followed.

In preferred embodiments, the hydrocarbon is incorporated into the center portion of the gum, while the *magnolia* extract is included in a gum coating. For instance, in certain embodiments, the hydrocarbon is incorporated into a center layer of the gum, or is center filled, using any suitable technique known in the art, while the *magnolia* extract is incorporated into a coating syrup or coating flavor, such as described hereinafter.

Chewing gum base and chewing gum product have been manufactured conventionally using separate mixers, different mixing technologies and, often, at different factories. One reason for this is that the optimum conditions for manufacturing gum base, and for manufacturing chewing gum from gum base and other ingredients such as sweeteners and flavors, are so different that it has been impractical to integrate both tasks. Chewing gum base manufacturing involves the dispersive (often high shear) mixing of difficult-to-blend ingredients, such as elastomer, filler, elastomer plasticizer, base softeners/emulsifiers, and sometimes waxes. This process typically requires long mixing times. Chewing gum product manufacture also involves combining the gum base with more delicate ingredients such as product softeners, bulk sweeteners, high intensity sweeteners and flavoring agents using distributive (generally lower shear) mixing, for shorter periods.

Chewing gums of the present invention may also be coated. Pellet or ball gum is prepared as conventional chewing gum, but formed into pellets that are pillow shaped, or into balls. The pellets/balls can be then sugar coated or panned by conventional panning techniques to make a unique sugar coated pellet gum.

Conventional panning procedures generally coat with sucrose, but recent advances in panning have allowed the use of other carbohydrate materials to be used in the place of sucrose. Some of these components include, but are not limited to, dextrose, maltose, palatinose, xylitol, lactitol, hydrogenated isomaltulose and other new alditols or a combination thereof. These materials may be blended with panning modifiers including, but not limited to, gum arabic, maltodextrins, corn syrup, gelatin, cellulose type materials like carboxymethyl cellulose or hydroxymethyl cellulose, starch and modified starches, vegetable gums like alginates, locust bean gum, guar gum, and gum tragacanth, insoluble carbonates like calcium carbonate or magnesium carbonate and talc. Antitack agents may also be added as panning modifiers which allow the use of a variety of carbohydrates and sugar alcohols to be used in the development of new panned or coated gum products. Essential oils may also be added with the sugar coating with *magnolia* extract to yield unique product characteristics.

The *magnolia* extract alone or in combination with the hydrocarbon can be easily added to a hot sugar solution prepared for sugar panning. In another embodiment, *magnolia* extract can also be used as a powder alone or blended with a powdered hydrocarbon and used in conventional panning procedures.

Candies/Confectionaries

As previously discussed, the oral compositions of the present disclosure may alternatively be in the form of a confectionery product, including for example hard candies, chewy candies, coated chewy center candies, tableted candies, chocolates, nougats, dragees, confectionery pastes and the like. These candies or confectionery products may comprise any of the various sugars and sweeteners, flavoring agents and/or colorants, as well as other components, known in the art and/or set forth above in the discussion of chewing gums. Additionally, these candies or confectionery products may be prepared using processing conditions and techniques known in the art. The candies or confectionery products may include the *magnolia* extract and hydrocarbon in any of the amounts set forth herein. In one particular embodiment, the candies or confectionery products may comprise up to about 0.2% by weight of *magnolia* extract and about 2.0% by weight of hydrocarbon.

By way of example, a hard candy can be primarily comprised of corn syrup and sugar, and derives its name from the fact that it contains only between 1.0% and 4% by weight moisture. In appearance, these types of candies are solid, but they are actually supercooled liquids, which are far below their melting points. There are different types of hard candies. Glass types are usually clear or made opaque with dyes; and grained types, which are always opaque, due to entrapped air and/or moisture.

For illustrative purposes, it is to be noted that a continuous making process for making deposited glass types, with a sugar base can be generally as follows. Sugar corn syrup mixture is spread over a cylinder heated by high pressure steam. Rapid head exchange causes the water in the syrup to evaporate. The cooked syrup is discharged, colors and flavors are added. These can be conveyed directly to hoppers which then discharge directly into molds. The candy is conveyed to batch rollers, which shapes and sizes the batch. The candy enters a former, which shapes the individual pieces into discs, balls, barrels, etc. The present disclosure can be made into any shape, circles, squares, triangles etc., also into animal shapes or any other novelty molding available. The candy is then cooled, wrapped and packaged.

For grained types of candy, water and sugar are the basic components being mixed with other ingredients, and cooked at high temperatures (290° F. to 310° F.), causing the water to turn to steam. The product is transferred to a cooling wheel, where it is collected in about 150 pound batches, placed in a pulling machine to aerate the product, and the flavor is added. The candy is transferred to batch rollers where it is shaped and sized. The candy then enters a former, which shapes the individual pieces. The candy is cooled at a relative humidity of 35% and enters a rotating drum where it is coated with a fine sugar. The candy is then conveyed to the graining room for four hours at 90° F. and 60% humidity. The entrapped air and moisture causes the product to grain. The *magnolia* extract and hydrocarbon may be added at any suitable point during the manufacturing process, and typically during addition of the flavors.

Alternative Forms

In some embodiments, the oral composition may be a lozenge, bead, tablet, or capsule. The lozenge, bead, tablet, or capsule may include the *magnolia* extract and hydrocarbon in any of the amounts set forth herein. In one particular embodiment, the lozenge, bead, tablet, or capsule may comprise up to about 0.2% by weight of *magnolia* extract and about 2.0% by weight of hydrocarbon. The orally acceptable vehicle or carrier used to form a lozenge, bead, tablet, or capsule is typically a non-cariogenic, solid water-soluble polyhydric alcohol (polyol) such as mannitol, xylitol, sorbitol, maltitol, erythritol, hydrogenated starch hydrozylate (HSH), hydrogenated glucose, hydrogenated disaccharides or hydrogenated polysaccharides, in an amount of about 85 to about 95% by weight of the total composition. Emulsifiers such as glycerin, and tableting lubricants, in minor amounts of about 0.1 to 5% by weight, may be incorporated into the tablet, bead, lozenge, or capsule formulation to facilitate the preparation of the tablet, beads, capsules, and lozenges. Suitable lubricants include vegetable oils such as coconut oil, magnesium stearate, aluminum stearate, talc, starch and polyethylene glycols. Suitable noncariogenic gums include kappa carrageenan, carboxymethyl cellulose, hydroxyethyl cellulose and the like.

A lozenge, bead, tablet, or capsule may optionally be coated with a coating material such as waxes, shellac, carboxymethyl cellulose, polyethylene/maleic anhydride copolymer or kappa-carrageenan to further increase the time it takes the tablet or lozenge to dissolve in the mouth. The uncoated tablet or lozenge is slow dissolving, providing a sustained release rate of active ingredients of about 3 to 5 minutes. Accordingly, the solid dose tablet, bead and lozenge compositions of this embodiment affords a relatively longer time period of contact of the teeth in the oral cavity with the *magnolia* extract of the present invention.

In some embodiments, the oral composition is a lozenge or capsule. The lozenge or capsule may comprise an oil-based core comprising the hydrocarbon, and a coating, such as described herein, comprising the *magnolia* extract. By incorporating the *magnolia* extract into the coating and the hydrocarbon into the core of the lozenge, the cell surface hydrophobicity of oral bacteria is affected prior to contact with the hydrocarbon, resulting in preferential removal from the oral cavity of the affected bacteria.

In other embodiments, the *magnolia* extract is included in the oil-based core. In one embodiment, the oral composition is a capsule comprising an oil-based core comprising the hydrocarbon and the *magnolia* extract. In general, the capsules contain a hydrocolloid. The hydrocolloid is a selected from a natural gum, a biosynthetic gum, a natural seaweed, a natural plant extrudate, a natural fiber extract, a gelatin, a biosynthetic process starch, a cellulosic material, an alginate, pectin, and combinations thereof.

In other embodiments, *magnolia* extract and a hydrocarbon, are "admixed" with or added to the complete chewing gum or confectionary composition. As used herein, "admixing," refers to the process where the *magnolia* extract and a hydrocarbon are mixed with or added to the completed composition or mixed with some or all of the components of the composition during product formation or some combination of these steps. When used in the context of admixing, the term "product" refers to the product or any of its components. This admixing step can include a process selected from the step of adding the *magnolia* extract and a hydrocarbon to the composition, spraying the *magnolia* extract and a hydrocarbon on the product, coating the *magnolia* extract and a hydrocarbon on the product, suspending the *magnolia* extract and a hydrocarbon in the product, painting the *magnolia* extract and a hydrocarbon on the product, pasting the *magnolia* extract and a hydrocarbon on the product, encapsulating the product with the *magnolia* extract and a hydrocarbon, mixing the *magnolia* extract and a hydrocarbon with the product and any combination thereof. The *magnolia* extract and the hydrocarbon may be admixed together or separately, and can be a liquid, dry powder, spray, paste, suspension or any combination thereof.

In another embodiment, the capsule containing the hydrocarbon and *magnolia* extract may be admixed with a chewing gum composition.

Mouth Rinse

In some embodiments, the oral composition is a mouth rinse. As used herein, the term "mouth rinse" refers to oral compositions that are substantially liquid in character, such as a mouth wash, spray, or rinse. In such a preparation, the oral composition typically has an aqueous phase comprising water or a water and alcohol mixture. Further, in various embodiments, the oral composition may comprise a humectant and surfactant as described below. Generally, the weight ratio of water to alcohol is in the range of in an amount of about 1:1 to about 20:1, preferably about 3:1 to 10:1 and more preferably about 4:1 to about 6:1. The total amount of water-alcohol mixture in this type of preparation is typically in an amount of about 70 to about 99.9% of the preparation. In various embodiments, the alcohol is typically ethanol or isopropanol.

The pH of such liquid and other preparations of the disclosure is generally in an amount of about 4.5 to about 10. The pH can be controlled with acid (e.g., citric acid or benzoic acid) or base (e.g., sodium hydroxide) or buffered (with sodium citrate, benzoate, carbonate, or bicarbonate, disodium hydrogen phosphate, or sodium dihydrogen phosphate, for example).

In various embodiments, the aqueous oral composition (e.g., mouth rinse) contains a humectant. The humectant is generally a mixture of humectants, such as glycerin and sorbitol, and a polyhydric alcohol such as propylene glycol, butylene glycol, hexylene glycol, polyethylene glycol. The humectant content is in the range of about 5 to about 40% and preferably about 10 to about 30%. Surfactants useful in this embodiment include anionic, nonionic, and zwitterionic surfactants. The surfactant is present in the aqueous oral compositions of the present disclosure in an amount of about 0.01% to about 5%, preferably in an amount of about 0.5% to about 2.5% by weight.

In embodiments where the oral composition is a mouth rinse, the *magnolia* extract may be added to the aqueous based mouth rinse, and the mouth rinse combined with an oil phase comprising the hydrocarbon. The oil phase may comprise the hydrocarbon only, or optionally may further include flavors, essential oils, any suitable antimicrobial actives (e.g., triclosan), or combinations thereof. The oil phase may make up about 0.05% to about 50% by weight of the mouth rinse. In some embodiments where the mouth rinse has a high concentration of oil, the mouth rinse may be a two phase rinse. In these embodiments, the rinse may be shaken prior to administration.

Animal Products

In some embodiments, the oral composition may be suitable for use by non-human mammals, and may be, for example, an animal treat (e.g., a biscuit).

Food products and supplements for animals are well known in the art and are preferably made with any suitable dough. Food supplement dough generally comprises at least one of flour, meal, fat, water, and optionally particulate proteinaceous particles (for texturization) and flavor. For instance, when the desired product is a biscuit, conventional dough can be used, optionally containing discrete particles of meat and/or meat by-products or farinaceous material. Examples of suitable dough for the production of hard and soft (including humectant for water control) animal biscuits are disclosed in U.S. Pat. Nos. 5,405,836; 5,000,943; 4,454,163; 4,454,164, the contents of each of which are incorporated herein by reference. Such compositions are preferably baked. The *magnolia* extract and hydrocarbon may be added with the flavor, included in an interior reservoir with a soft center, or coated onto the surface of a baked food supplement by dipping or spraying. Any other suitable means known to one of skill in the art for delivering active ingredients to animals may also be used.

This invention is illustrated, but not limited by, the following Examples.

EXAMPLES

Example 1: Microbial Adhesion to Hydrocarbons

In this example, the effect of MBE on the adherence of a wide array of Gram positive and Gram negative oral bacterial strains to the hydrocarbon hexadecane was examined using the kinetic Microbial Adhesion To Hydrocarbon (MATH) test.

Preparation of Bacterial Strains

Bacterial strains were grown on blood agar plates from frozen dimethylsulfoxide stocks, and subsequently inoculated in a 10 mL pre-culture of the appropriate liquid culture medium and environmental conditions. 100 µL of the pre-culture was used to inoculate 100 mL of fresh medium as the main culture.

*Streptococcus mutans* (ATCC 25175), *Streptococcus oralis* J22, *Streptococcus mitis* (ATCC 9811), *Streptococcus salivarius* HB, *Streptococcus sanguinis* (ATCC 10556) and *Streptococcus sobrinus* HG 1025 were grown aerobically at 37° C. in Todd-Hewitt broth (Oxoid, Basingstoke, UK). *Actinomyces naeslundii* T14V-J1, *Porphyromonas gingivalis* (ATCC 33277), *Prevotella intermedia* (ATCC 43046), *Veillonella parvula* BME1 and *Fusobacterium nucleatum* BME1 were grown anaerobically at 37° C. in Brain Heart Infusion (Oxoid, Basingstoke, UK) supplemented with sterile 0.5% haemin and 0.1% menadione. Bacteria were harvested by centrifugation at (1700 g) for 10 min and washed twice using sterile saliva buffer (1 mM calcium chloride, 2 mM potassium phosphate, 50 mM potassium chloride KCl, pH 6.8). Subsequently, the washed bacteria were used to create bacterial suspensions with different concentrations of MBE.

*Magnolia* Bark Extract

A 1% (w/v) solution of MBE powder (95% magnolol, 5% honokiol, Honsea Sunshine Biotech Co Ltd Guangzhou, China) in 100% ethanol was prepared. The solution was used to prepare solutions of MBE in sterile saliva buffer at concentrations of 25, 50, 100 and 200 µg/mL. Saliva buffer without MBE and saliva buffer with an equal amount of ethanol as the 200 µg/mL MBE solution were used as controls. All solutions were prepared fresh for every experiment. MBE powder was kept in the freezer at −20° C. for long term storage.

Microbial Adhesion to Hydrocarbons

The Microbial Adhesion to Hydrocarbons (MATH) test measures the hydrophobic nature of microbial cells in suspension by quantifying adherence to liquid hydrocarbons after short periods of mixing. The kinetic MATH test (previously described by Lichtenberg, et al., "A kinetic approach to bacterial adherence to hydrocarbons," J. Microbiol. Methods, 1985, Vol. 4, pp. 141-6) was used herein to quantify adherence.

First, 3 mL of bacterial suspension in saliva buffer was prepared in a glass tube for all MBE concentrations with an optical density at 600 nm ($A_0$) between 0.4 and 0.6 (representing approximately $4 \times 10^8$ and $6 \times 10^8$ bacterial cells) (Van der Mei, et al., "Hydrophobic and Electrostatic Cell Surface Properties of Thermophilic Dairy Streptococci," Appl. Environ. Microbiol., 1993, Vol. 59(12), pp. 4305-4312). Optical densities were measured using a spectrophotometer (Spectronic 20 Genesys, Thermo Scientific, Waltham Mass., USA) relative to saliva buffer without bacterial suspension and MBE. Subsequently, 150 µL of hexadecane was added to each glass tube and briefly mixed for 10 seconds using a vortex mixer set at a fixed rotation speed. The suspension was allowed to settle for 10 min for phase separation before optical density of the aqueous phase was measured again ($A_t$). This process was repeated 6 times to a total of 60 seconds of vortexing. Next, $\log(A_t/A_0 \times 100)$ was plotted against vortex time. Initial removal rate ($R_0$) was calculated as the slopes of tangent of the curve. $R_0$ represents bacterial removal rate per minute from the suspension to hexadecane, as a measure for cell surface hydrophobicity.

All experiments were performed in at least triplicates for each bacterial strain.

The removal rates of the Gram positive and the removal rates for the Gram negative strains for the different MBE concentrations were averaged. Subsequently data was analyzed for normality using Shapiro-Wilk and Kolmogorov-Smirnov tests (p<0.05) and equality of means was compared using an ANOVA followed by post-hoc analysis to identify differences between MBE concentrations. Statistical analysis was performed using SPSS v20.0 (IBM Corp., Armonk, USA).

Results

Figure 1A:
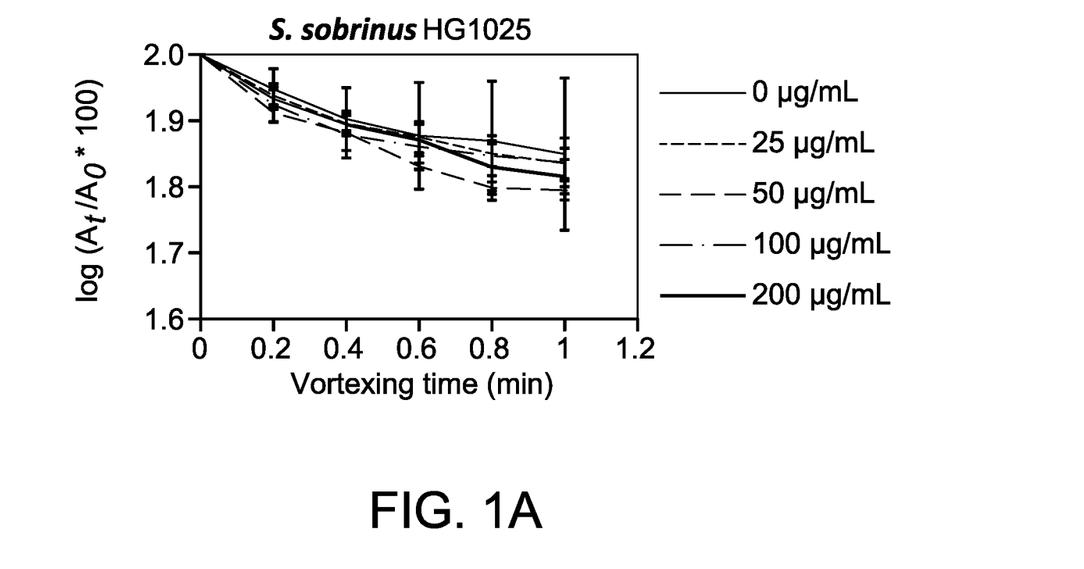
FIGS. 1A and 1B are graphs depicting the results of the kinetic MATH test described in Example 1, for the Gram positive bacteria *S. sobrinus* HG 1025 (FIG. 1A) and the Gram negative bacteria *P. gingivalis* (ATCC 33277) (FIG. 1B). Removal of oral bacteria at various concentrations of MBE from saliva buffer to hexadecane is expressed as $\log(A_t/A_0 \times 100)$ as a function of the vortexing time. Error bars represent standard error of the mean.
Figure 1B:
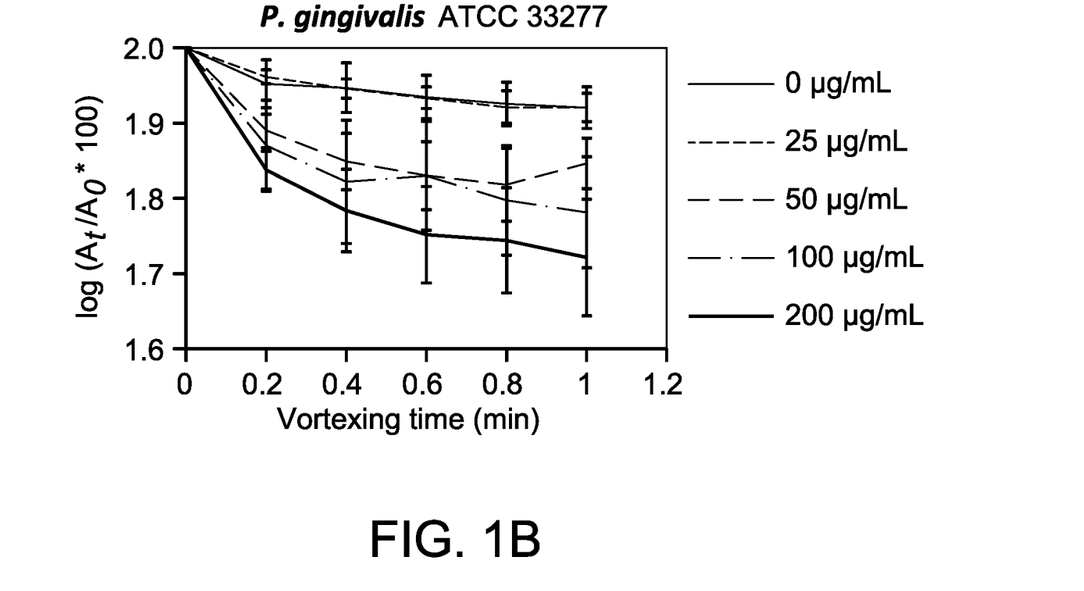
Figure 2:
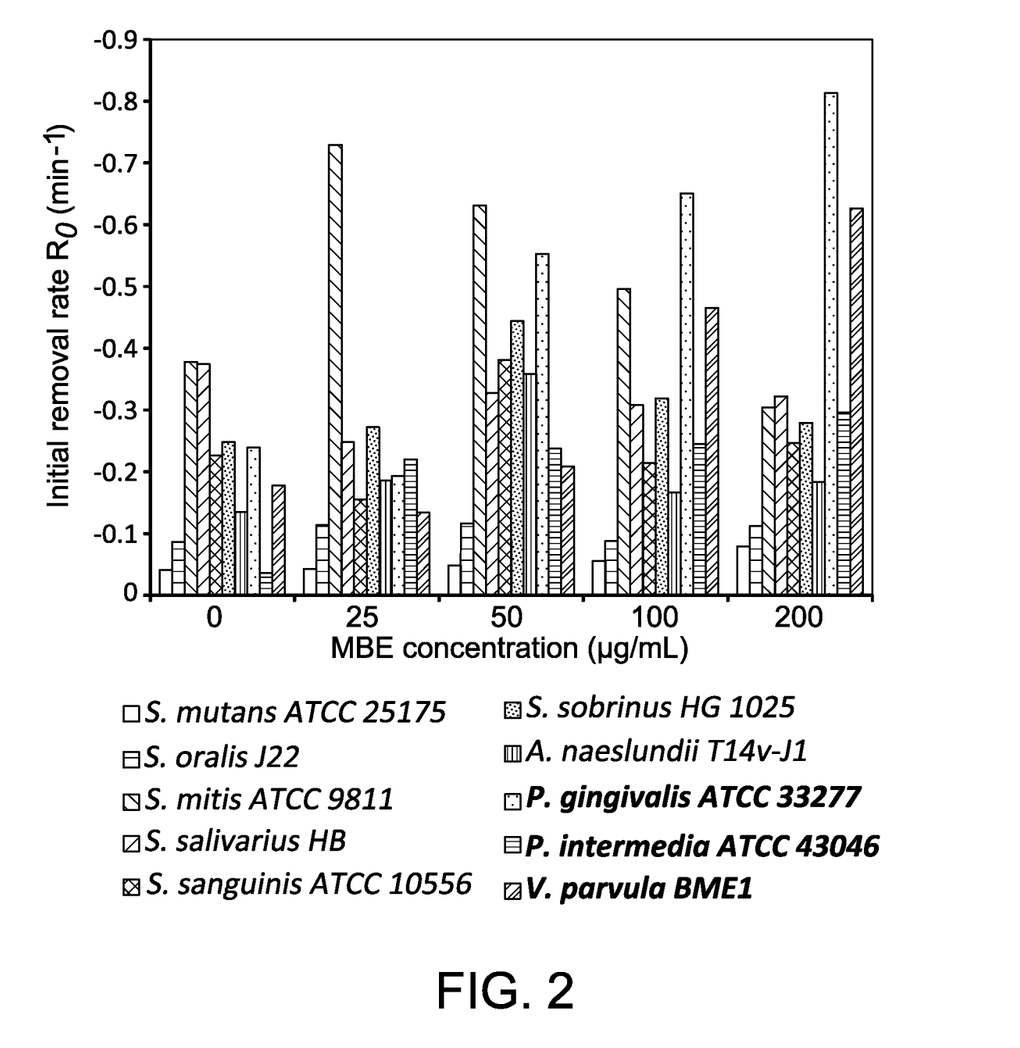
FIG. 2 is a chart depicting the cell surface hydrophobicity, expressed as removal rate per min by hexadecane ($R_0$ ($\min^{-1}$)), for 10 oral bacterial strains for 5 different concentrations of MBE. *V. parvula* BME1, *P. gingivalis* (ATCC 33277), and *P. intermedia* (ATCC 43046) are Gram negative strains.

The kinetic MATH test results showed a decrease in the optical density over vortexing time, indicating removal of bacteria from the saliva buffer to the hexadecane (see FIGS. 1A and 1B). The initial removal rate was dependent on the bacterial strain and also dependent on the concentration of MBE present in the solution. FIG. 2 displays $R_0$ values for all tested strains for various concentrations of MBE. Certain bacterial strains, such as *S. mutans* (ATCC 25175) and *S. oralis* J22, displayed relatively low removal rates while the removal rates for *S. mitis* (ATCC 9811) and *P. gingivalis* (ATCC 33277) were relatively high.

As can be seen from FIGS. 1 and 2, the removal rate for the *P. gingivalis* (ATCC 33277) strain is dependent on the concentration of the hydrophobic ligand MBE present in the solution, with a higher removal rate occurring at a higher concentration of MBE.

Removal rates were averaged for all Gram positive and all Gram negative strains, with the results shown in FIGS. 3A and 3B. As can be seen from FIG. 3B, the average removal rate of Gram negative bacteria significantly increased with increasing concentrations of MBE (increased from 0.15 to 0.57), while the average removal rate of Gram positive bacteria (FIG. 3A) was not influenced by the presence of MBE.

Figure 4:
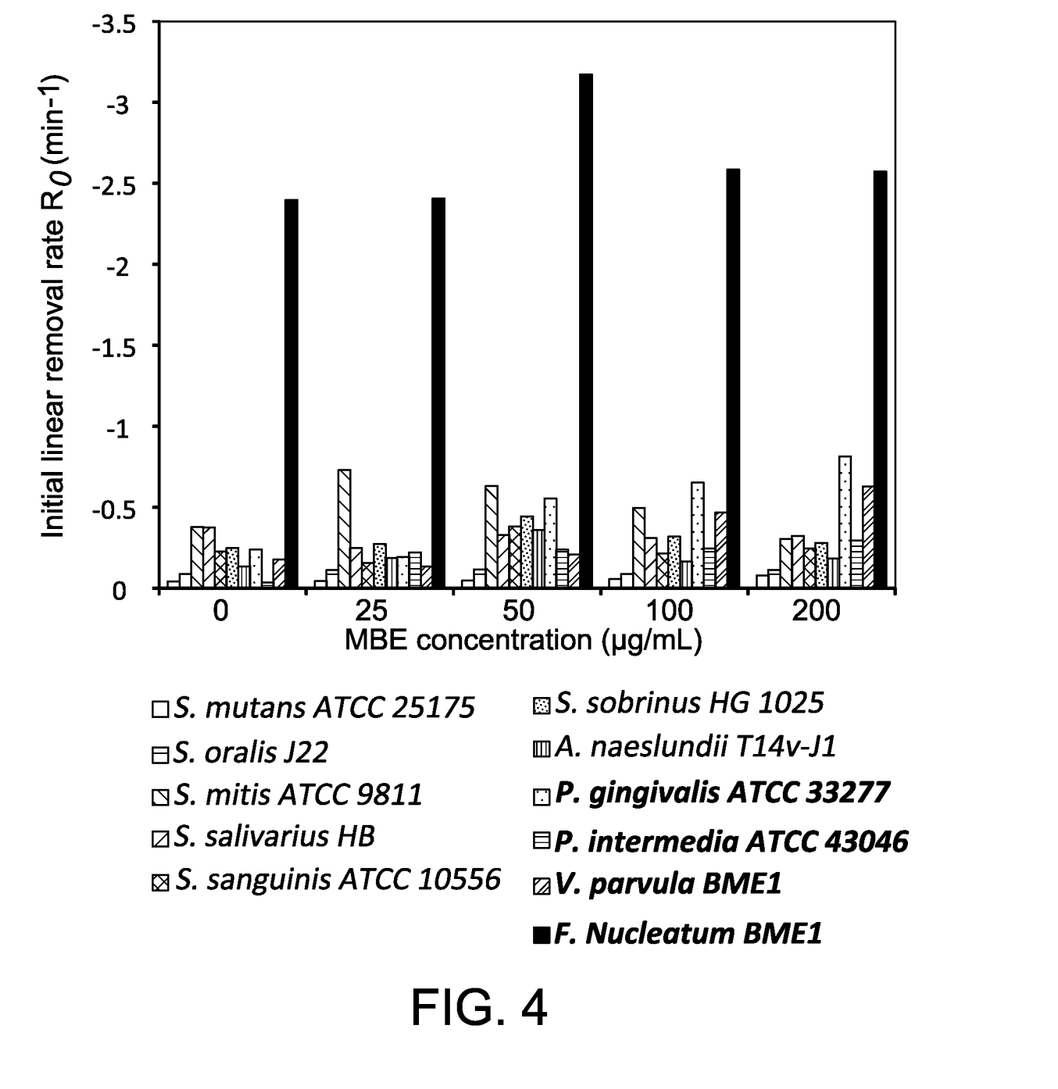
FIG. 4 is a chart comparing the cell surface hydrophobicity, expressed as removal rate per min by hexadecane ($R_0$ ($min^{-1}$)), for the 10 oral bacterial strains in FIG. 2 to that of the Gram negative bacteria *F. nucleatum* BME1.
Figure 5A:
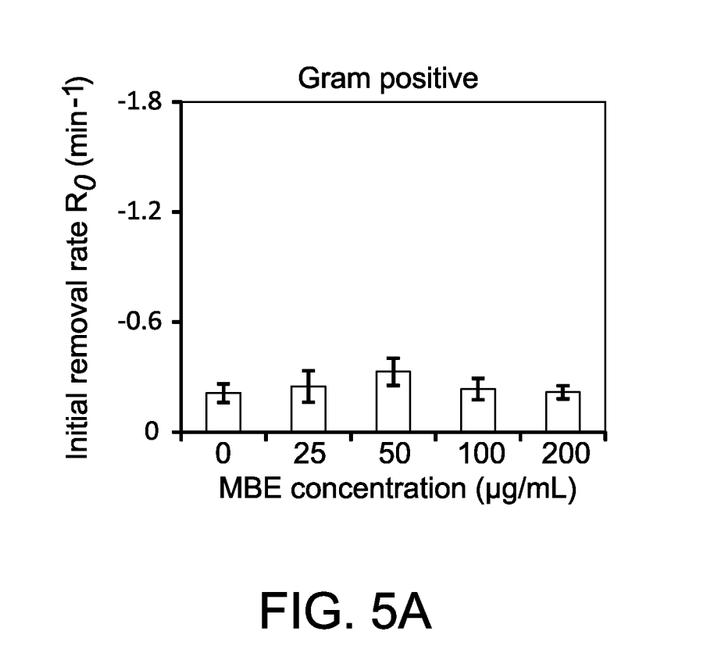
FIGS. 5A and 5B are charts depicting the cell surface hydrophobicity, expressed as removal rate per min by hexadecane ($R_0$ ($min^{-1}$)), averaged for all of the Gram positive (FIG. 5A) and Gram negative (FIG. 5B) bacteria depicted in FIG. 4. Error bars denote standard error of the mean.
Figure 5B:
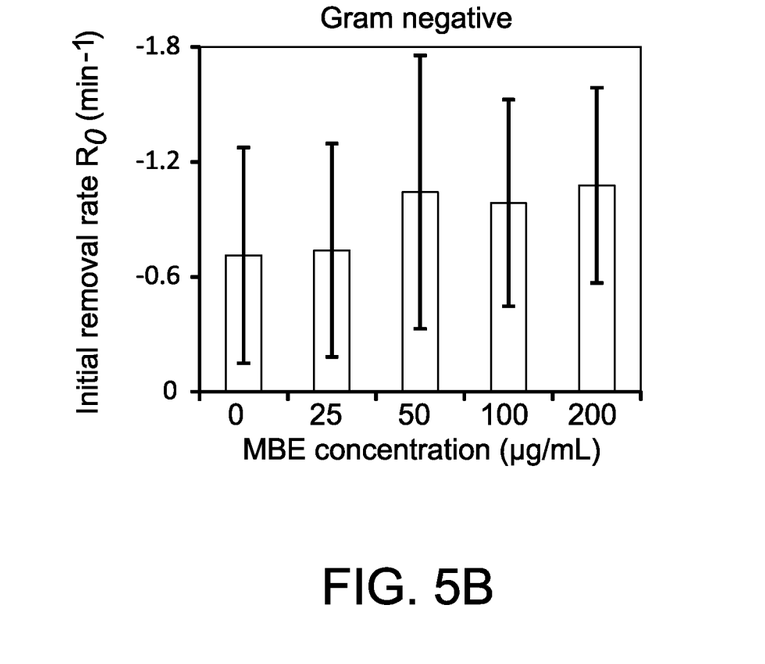

The $R_0$ values for the Gram negative *F. nucleatum* were not included in FIGS. 2 and 3, since this strain is highly hydrophobic ($R_0 = -2.4$) and skewed the results. For comparison, the results, including those from *F. nucleatum*, are depicted in FIGS. 4 and 5.

It should be noted that although the average removal rate of Gram positive bacteria was not influenced by the presence of MBE, there was a low, but significant, increase in removal rate for *S. mutans* (ATCC 25175) (from 0.04 to 0.08) with increasing concentration of MBE (see FIG. 2). This increase is similar to a previously demonstrated increase in removal rate of *S. mutans* (ATCC 10449) by triclosan (from 0.01 to 0.05), which was shown to invoke a change in biofilm composition (see Jongsma, et al., *Int. J. Oral Sci.*, 2015, Vol. 7, pp. 42-48). These results thus suggest that *magnolia* extract can be used for the removal of *S. mutans* strains from the oral cavity.

Example 2: Microbial Adhesion to Hydrocarbons

In this example, the effect of MBE on the adherence of the Gram negative bacteria *Porphyromonas gingivalis* and *Fusobacterium nucleatum* to limonene or medium chain triglyceride (MCT) oil was examined using optical density (OD) measurements and viable colony count.

Preparation of Bacterial Strains

*P. gingivalis* (ATCC33277) was grown anaerobically in THB broth supplemented with 0.001% hemin and 0.0001% Vitamin K. *F. nucleatum* (ATCC10953) was grown anaerobically in Schaelder broth supplemented with 0.001% hemin and 0.0001% Vitamin K. For viable colony counting, anaerobic blood agar plates were used.

Test bacterial suspensions ($OD_{550} = 0.6$) in saliva buffer were prepared for experiments. When anaerobic test bacteria were used, care was taken to minimize exposure to atmospheric oxygen and operation was performed in the anaerobic chamber as much as possible. The saliva buffer was pre-reduced in the anaerobic chamber to remove oxygen.

Capsules

Capsules containing a hydrocarbon and MBE in the core were used in this example. Capsule A had a core comprising approximately 150 µL of limonene oil and MBE (96 wt. % food grade limonene oil and 4 wt. % MBE), and Capsule B had a core comprising approximately 150 µL of MCT oil and MBE (96 wt. % MCT oil (NEOBEE® M-5), and 4 wt. % MBE).

Optical Density and Viable Colony Count Measurements

First, 2 mL of saliva buffer was placed in a glass tube (16×100 mm), and three pieces of Capsule A or B were added. The tubes with mixtures were incubated at 45° C. for 10 minutes and transferred to the anaerobic chamber. One milliliter of the test bacterial suspension was added to each tube inside the anaerobic chamber and all tubes were sealed with paraffin.

All tubes were then removed from the chamber and vortexed six times at 10 seconds each, with a 20 second interval, for a total vortex time of 60 seconds. After standing at room temperature for 10 minutes, the optical density at 550 nm ($OD_{550}$) of the aqueous phase of the test suspension was measured. Buffer containing Capsule A or B was used as a blank.

In addition to optical density measurements, the numbers of bacteria present in the lower phase of the mixture (aqueous phase) were also determined by viable colony count of the cell suspension. The latter was serially diluted and plated on CDC anaerobic blood agar plates. All plates were incubated anaerobically for 2-7 days until visible colonies appeared and CFU/mL were enumerated.

Results

The effects of the MBE and oil containing capsules on *P. gingivalis* and *F. nucleatum* are shown in Tables 1 and 2 below.

TABLE 1

Effect of Capsules A and B on *P. gingivalis* and *F. nucleatum*

| | | | $OD_{550}$ | average | % control | CFU/ml | average | % |
|---|---|---|---|---|---|---|---|---|
| *F. nucleatum* | control | 1 | 0.268 | 0.266 | 100 | $1.2 \times 10^6$ | $1.2 \times 10^6$ | 100 |
| | | 2 | 0.266 | | | $1.3 \times 10^6$ | | |
| | | 3 | 0.264 | | | $1.0 \times 10^6$ | | |
| | Capsule A | 1 | 0.126 | 0.017 | 6.85 | 0 | 0 | |
| | | 2 | −0.029 | | | 0 | | |
| | | 3 | −0.046 | | | 0 | | |
| | Capsule B | 1 | 0.343 | 0.177 | 71.3 | $5.6 \times 10^5$ | $4.7 \times 10^5$ | 39.62 |
| | | 2 | 0.147 | | | $3.3 \times 10^5$ | | |
| | | 3 | 0.041 | | | $5.0 \times 10^6$ | | |
| *P. gingivalis* | control | 1 | 0.282 | 0.282 | 100 | NG* | | |
| | | 2 | 0.281 | | | NG | | |
| | | 3 | 0.282 | | | NG | | |
| | Capsule A | 1 | 0.340 | 0.261 | 93.3 | NG | | |
| | | 2 | 0.278 | | | NG | | |
| | | 3 | 0.164 | | | NG | | |
| | Capsule B | 1 | 0.171 | 0.191 | 68.5 | NG | | |
| | | 2 | 0.209 | | | NG | | |
| | | 3 | 0.194 | | | NG | | |

*NG: no growth

As can be seen from these results, Capsule A removed most of the *F. nucleatum* from the lower aqueous phase, since no growth was observed as measured by viable colony count. The optical density readings also demonstrated a reduction of about 93% of *F. nucleatum* by Capsule A. Because *P. gingivalis* did not grow (even in the control), the experiment was repeated, and the results set forth below in Table 2.

TABLE 2

Effect of Capsules A and B on *P. gingivalis* and *F. nucleatum*

| | | | $OD_{550}$ | average | % control | CFU/ml | average | % control |
|---|---|---|---|---|---|---|---|---|
| *F. nucleatum* | control | 1 | 0.243 | 0.240 | 100 | $1.6 \times 10^7$ | $1.4 \times 10^7$ | 100 |
| | | 2 | 0.238 | | | $1.0 \times 10^7$ | | |
| | | 3 | 0.240 | | | $1.5 \times 10^7$ | | |
| | Capsule A | 1 | 0.409 | 0.432 | 180 | $2.0 \times 10^5$ | $1.9 \times 10^5$ | 1.4 |
| | | 2 | 0.371 | | | $1.9 \times 10^5$ | | |
| | | 3 | 0.516 | | | $1.8 \times 10^6$ | | |
| | Capsule B | 1 | 0.719 | 0.679 | 282.8 | $5.5 \times 10^5$ | $5.4 \times 10^6$ | 39.75 |
| | | 2 | 0.700 | | | $5.6 \times 10^6$ | | |
| | | 3 | 0.617 | | | $5.1 \times 10^6$ | | |
| *P. gingivalis* | control | 1 | 0.216 | 0.210 | 100 | $2.2 \times 10^8$ | $1.9 \times 10^8$ | 100 |
| | | 2 | 0.208 | | | $2.3 \times 10^8$ | | |
| | | 3 | 0.207 | | | $1.3 \times 10^8$ | | |
| | Capsule A | 1 | 0.360 | 0.200 | 95.08 | $4.7 \times 10^4$ | $1.7 \times 10^5$ | 0.09 |
| | | 2 | 0.211 | | | $1.0 \times 10^5$ | | |
| | | 3 | 0.028 | | | $3.1 \times 10^5$ | | |
| | Capsule B | 1 | 0.306 | 0.208 | 98.89 | $3.7 \times 10^8$ | $4.2 \times 10^8$ | 221 |
| | | 2 | 0.205 | | | $4.0 \times 10^8$ | | |
| | | 3 | 0.112 | | | $5.0 \times 10^8$ | | |

Consistent with the data set forth in Table 1, the data in Table 2 shows that Capsule A removed most of the *F. nucleatum* from the aqueous phase, as evidenced by the reduction in detectable viable colony count of greater than 98%. Capsule A also removed greater than 99% of *P. gingivalis* from the aqueous phase, as measured by viable colony count. Capsule B removed *F. nucleatum* from the aqueous phase, as evidenced by reduction in viable colony count of about 60%.

Although the optical density measurements set forth in Table 1 demonstrated a reduction of E *nucleatum* by Capsule A of about 93%, the Table 2 data did not reflect this reduction. Without wishing to be bound to any particular theory, this fluctuation in optical density measurements may be explained by interference in the optical density readings resulting from the blue color of the capsules after dissolving in buffer, and the presence of insoluble particles in the suspension.

Since both Capsules A and B were blue in color, and granules could frequently be observed when the capsules were mixed with buffer, the results set forth in Tables 1 and 2 were confirmed using the oil and MBE content present in the capsules. For this test, a total of 150 μL of the oil content was withdrawn from either Capsule A or B for testing using optical density and viable colony count measurements. The results are set forth below in Table 3.

TABLE 3

Effect of Oil/MBE Withdrawn from Capsules A and B on *P. gingivalis* and *F. nucleatum*

| | | | $OD_{550}$ | average | % control | CFU/ml | average | % |
|---|---|---|---|---|---|---|---|---|
| *F. nucleatum* | control | 1 | 0.256 | 0.242 | 100 | $4.6 \times 10^5$ | $6.1 \times 10^5$ | 100 |
| | | 2 | 0.234 | | | $6.9 \times 10^5$ | | |
| | | 3 | 0.235 | | | $6.8 \times 10^5$ | | |
| | Capsule A | 1 | 0.215 | 0.199 | 82.48 | $5.6 \times 10^4$ | $5.2 \times 10^4$ | 8.65 |
| | | 2 | 0.196 | | | $4.9 \times 10^4$ | | |
| | | 3 | 0.187 | | | $5.4 \times 10^4$ | | |
| | Capsule B | 1 | 0.281 | 0.259 | 107.17 | $4.0 \times 10^5$ | $3.9 \times 10^5$ | 63.45 |
| | | 2 | 0.254 | | | $3.9 \times 10^5$ | | |
| | | 3 | 0.242 | | | $3.7 \times 10^6$ | | |
| *P. gingivalis* | control | 1 | 0.185 | 0.185 | 100 | $1.3 \times 10^8$ | $1.8 \times 10^8$ | 100 |
| | | 2 | 0.192 | | | $1.5 \times 10^8$ | | |
| | | 3 | 0.179 | | | $2.6 \times 10^8$ | | |
| | Capsule A | 1 | 0.171 | 0.151 | 81.29 | NA | No colony on lowest dilution | NA |
| | | 2 | 0.150 | | | NA | | |
| | | 3 | 0.131 | | | NA | | |
| | Capsule B | 1 | 0.245 | 0.226 | 122.12 | $3.4 \times 10^7$ | $4.2 \times 10^7$ | 23.25 |
| | | 2 | 0.235 | | | $3.9 \times 10^7$ | | |
| | | 3 | 0.199 | | | $5.3 \times 10^7$ | | |

As can be seen from Table 3, the oil/MBE from Capsule A removed greater than 90% of *F. nucleatum* and greater than 99% of *P. gingivalis* from the aqueous phase, as measured by viable colony count, while the oil/MBE from Capsule B removed greater than 35% of *F. nucleatum* and greater than 75% of *P. gingivalis* from the aqueous phase, as measured by viable colony count. These results confirm the data set forth in Tables 1 and 2 that Capsules A and B are effective at removing *F. nucleatum* and *P. gingivalis* from the aqueous phase, and suggest that the combination of MBE and limonene or MCT oil may be effective at removing *F. nucleatum* and *P. gingivalis* from the oral cavity.

Example 3: Chewing Gum Compositions

In this example, chewing gum compositions containing *magnolia* extract and hydrocarbons are prepared according to the following formulas, using conventional procedures.

Gum Center

| Ingredients | A (weight %) | B (weight %) | C (weight %) |
|---|---|---|---|
| Gum Base | 28.00 | 34.05 | 25.00 |
| Sorbitol | 59.998 | 54.80 | 57.36 |
| Mannitol | 1.00 | — | 3.00 |
| Lycasin/Glycerin | 8.44 | 8.00 | 12.00 |
| Sweetener | 0.80 | 0.80 | 0.80 |
| Flavor | 1.75 | 1.75 | 1.75 |
| *Magnolia* Extract | 0.002 | — | — |
| Limonene | 0.01 | — | 0.02 |
| Myrcene | — | 0.60 | — |
| Lycopene | — | — | 0.05 |
| Sesquiterpene | — | — | 0.02 |
| TOTAL | 100.00 | 100.00 | 100.00 |

Coating

| Ingredients | D (weight %) | E (weight %) | F (weight %) |
|---|---|---|---|
| Maltitol | — | 70.29 | — |
| Isomalt | — | — | 68.00 |
| Xylitol | 62.808 | — | — |
| Mannitol | 1.00 | — | 3.00 |
| Gum Acacia | 8.44 | 5.70 | 12.00 |
| Calcium Carbonate | 23.00 | 19.90 | 12.36 |
| High potency sweetener | 0.80 | 0.80 | 0.80 |
| Flavor | 1.75 | 1.00 | 1.75 |
| *Magnolia* Extract | 0.002 | 0.30 | 0.09 |
| Wax | 1.00 | 1.00 | 1.00 |
| Color | 1.00 | 1.00 | 1.00 |
| Lycopene | 0.20 | — | — |
| Linoleic acid | — | 0.01 | — |
| TOTAL | 100.00 | 100.00 | 100.00 |

In an embodiment, the gum center of formula A may be coated with the coating of any of formulas D, E, or F using any suitable technique. In another embodiment, the gum of formula B may be coated with the coating of any of formulas D, E, or F using any suitable technique. In another embodiment, the gum of formula C may be coated with the coating of any of formulas D, E, or F using any suitable technique.

Example 4: Hard Candy

In this example, a hard candy containing *magnolia* extract and hydrocarbons is prepared according to the following formula, using conventional procedures.

| Ingredients | Weight % |
|---|---|
| Isomalt | 97.83 |
| Xylitol | 1.05 |
| High intensity sweetener | 0.07 |
| Flavor | 0.04 |
| Lycopene | 1.00 |
| *Magnolia* Bark Extract | 0.01 |

Example 5: Compressed Mint

In this example, a compressed mint containing *magnolia* extract and hydrocarbon is prepared according to the following formula, using conventional procedures.

| Ingredients | Weight % |
| --- | --- |
| Polyol Bulking Agent | 94-98% |
| Magnesium Stearate | 0.6-0.8% |
| *Magnolia* Extract | 0.01-0.50% |
| Flavors | 0.1-0.2% |
| Hydrocarbon | 0.001-2.0% |

Example 6: Dog Biscuit

In this example, a dog biscuit containing *magnolia* extract and hydrocarbon is prepared according to the following formula, using conventional procedures.

| Ingredients | Weight % |
| --- | --- |
| Ground Wheat | 30.0 |
| Oats & Bran | 17.0 |
| Grits & Seeds | 16.5 |
| Gluten | 7.5 |
| Sugar | 6.0 |
| Fat | 5.0 |
| Aromas, Flavors | 7.5 |
| Vitamins & Minerals | 9.95 |
| Sesquiterpene | 0.50 |
| *Magnolia* Bark Extract | 0.05 |

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An oral composition for freshening breath, the oral composition comprising from about 0.001% to about 0.5% by weight of *magnolia* extract and from about 0.001% to about 2.0% by weight of hydrocarbon, wherein the hydrocarbon is hexadecane; and wherein the composition effectively removes one or more oral bacteria from the oral cavity, wherein the oral bacteria is selected from the group consisting of: *S. mutans, P. gingivalis, F. nucleatum*, and combinations thereof.

2. The composition of claim 1, wherein the composition reduces the adherence of plaque to teeth.

3. The composition of claim 1, wherein the composition is selected from the group consisting of chewing gums, confections, tablets, beads, lozenges, capsules, and a mouth rinse.

4. The composition of claim 1, wherein the composition is an animal treat biscuit.

5. The composition of claim 1, wherein the *magnolia* extract comprises from about 2% to about 99% by weight of a hydrophobic ingredient selected from the group consisting of magnolol, honokiol, and combinations thereof.

6. The composition of claim 1, wherein the composition comprises from about 0.5% to about 2.0% by weight of the hexadecane.

* * * * *